(12) United States Patent
    Wang

(10) Patent No.: US 10,238,551 B2
(45) Date of Patent: Mar. 26, 2019

(54) SYSTEM AND METHODS FOR MONITORING DEFECATION, URINATION, NEAR-BODY TEMPERATURE, BODY POSTURE AND BODY MOVEMENTS IN YOUNG CHILDREN, PATIENTS AND ELDERLIES

(71) Applicant: Mavin Wear Inc., San Jose, CA (US)

(72) Inventor: Lu Wang, San Jose, CA (US)

(73) Assignee: MAVIN WEAR INC., San Jose, CA (US)

( * ) Notice: Subject to any disclaimer, the term of this patent is extended or adjusted under 35 U.S.C. 154(b) by 0 days.

(21) Appl. No.: 15/230,176

(22) Filed: Aug. 5, 2016

(65) Prior Publication Data
US 2017/0035622 A1   Feb. 9, 2017

Related U.S. Application Data

(60) Provisional application No. 62/202,718, filed on Aug. 7, 2015.

(51) Int. Cl.
*A61F 13/42*   (2006.01)

(52) U.S. Cl.
CPC ........ *A61F 13/42* (2013.01); *A61F 2013/421* (2013.01); *A61F 2013/423* (2013.01); *A61F 2013/424* (2013.01)

(58) Field of Classification Search
CPC .............................. A61F 13/42; A61B 5/6808

USPC ....................................................... 340/573.5
See application file for complete search history.

(56) References Cited

U.S. PATENT DOCUMENTS

| | | | |
|---|---|---|---|
| 2005/0274629 A1* | 12/2005 | Lin ..................... | G01N 33/5438 205/777.5 |
| 2007/0252713 A1* | 11/2007 | Rondoni ................ | A61B 5/202 340/573.5 |
| 2014/0121473 A1* | 5/2014 | Banet ................... | A61B 5/6808 600/301 |
| 2014/0163343 A1* | 6/2014 | Heneghan ............ | A61B 5/0507 600/324 |
| 2014/0327546 A1* | 11/2014 | Carney .................. | A61F 13/42 340/573.5 |
| 2014/0333442 A1* | 11/2014 | Carney ............. | H04M 1/72527 340/573.5 |
| 2015/0157512 A1* | 6/2015 | Abir ....................... | A61F 13/42 340/573.5 |
| 2016/0120453 A1* | 5/2016 | Pop ........................ | A61B 5/204 600/437 |

\* cited by examiner

*Primary Examiner* — Fabricio R Murillo Garcia
(74) *Attorney, Agent, or Firm* — Wilson Sonsini Goodrich & Rosati

(57) ABSTRACT

Remotely detecting the presence of urine or feces in a diaper of an infant or adult using a disposable sensor placed inside the diaper, in conjunction with a permanent device that is capable of wirelessly transmitting data to a mobile device or base station is disclosed. The permanent device can also be capable of measuring temperature and body movements. This additional information can be used in conjunction with the detection of urine or feces to identify patterns.

19 Claims, 10 Drawing Sheets

SYSTEM AND METHODS FOR MONITORING DEFECATION, URINATION, NEAR-BODY TEMPERATURE, BODY POSTURE AND BODY MOVEMENTS IN YOUNG CHILDREN, PATIENTS AND ELDERLIES

CROSS REFERENCE TO RELATED APPLICATION

This application claims the benefit under 35 U.S.C. § 119(e) of U.S. Provisional Patent Application No. 62/202,718, filed Aug. 7, 2015; the content of which is incorporated by reference herein in its entirety for all intended purposes.

FIELD OF THE DISCLOSURE

This relates generally to a system and methods for monitoring defecation, urination, near-body temperature, body posture, and body movements.

BACKGROUND OF THE DISCLOSURE

Nearly four million infants are born in the United States every year. Infants are frequently in need of monitoring, especially when they are out-of-sight from their parents or caregivers. Devices such as baby monitors are thus helpful, if not essential, to parents and caretakers in caring for and ensuring the safety of their babies. Traditional baby monitors, however, typically only capture sound and/or video. They fail to monitor a baby's other vital signs and conditions.

On the other side of the age spectrum, aging populations are becoming more prevalent in societies, such as those in the United States, Europe, China, India, and Japan. As of 2012, long-term care service providers (including adult day services centers, home health agencies, hospices, nursing homes, and residential care communities) served approximately 8,357,100 people annually in the United States. Many of these adults who receive long-term care services are also in need of constant monitoring and benefit from devices similar to baby monitors.

Approximately 27.4 billion diapers are used in the United States each year. A common feature in many disposable diapers is a wetness indicator that will react to liquid exposure and visibly change color. The capability of detecting the presence of urine remotely without having to look at the diaper, however, is limited. Also limited is the ability of diapers to detect feces, which may not visibly change the color of a wetness indicator. In addition, the capability of detecting the presence of feces without having to smell the diaper is limited.

BRIEF SUMMARY OF THE DISCLOSURE

The disclosure relates to monitoring defecation, urination, near-body temperature and other vital signs, body posture, body movements and other physiological data of infants, patients, elderly individuals, and special needs individuals, and communicating the information via wireless technology or other communication means to mobile devices, base stations, or other electronics capable of receiving and processing the information. A system according to examples of the disclosure can include one or more of the following: (1) a permanent device that can be mounted to a diaper or clothing, (2) a disposable or reusable sensor that can be placed inside a diaper or clothing, and (3) a receiving device capable of receiving signals from the permanent device. The permanent device can be capable of detecting body temperature or other vital signs, posture, and movement, among other things. Sensors such as thermistors, thermocouples, infrared temperature readers, or other sensing mechanisms can be used to detect near-body temperature and other vital signs continually or periodically, and motion-sensing devices such as gyroscopes or accelerometers can be used to detect body posture and movements. One or more algorithms can be used to distinguish larger body movements, such as tossing and turning, from smaller movements, such as breathing. In some examples, the disposable or reusable sensor can monitor the presence of feces and/or urine by detecting an impedance between one or more electrode arrays within the disposable sensor. The data recorded by the permanent device and disposable sensor can be stored and transmitted to a mobile device, base station or other electronic device. Parents and caretakers can not only use the instant information to attend to the needs of infants, patients, elderly and special needs individuals, but stored data can also be used to identify certain patterns such as defecation or urination frequency or sleep cycles and sleep quality.

DETAILED DESCRIPTION OF THE INVENTION

In the following description of examples, reference is made to the accompanying drawings which form a part hereof, and in which it is shown by way of illustration specific examples that can be practiced. It is to be understood that other examples can be used and structural changes can be made without departing from the scope of the disclosed examples.

The disclosure relates to monitoring defecation, urination, near-body temperature and other vital signs, body posture, body movements and other physiological data of infants, patients, and individuals, and special needs individuals, and communicating the information via wireless technology or other communication means to mobile devices, base stations, or other electronics capable of receiving and processing the information. A system according to examples of the disclosure can include one or more of the following: (1) a permanent device that can be mounted to a diaper or clothing, (2) a disposable or reusable sensor that can be placed inside a diaper or clothing, and (3) a receiving device capable of receiving signals from the permanent device. The permanent device can be capable of detecting body temperature or other vital signs, posture, and movement, among other things. Sensors such as thermistors, thermocouples, infrared temperature readers, or other sensing mechanisms can be used to detect near-body temperature and other vital signs continually or periodically. Gyroscopes or accelerometers or other motion-sensing devices can be used to detect body posture and movements. One or more algorithms can be used on data gathered from gyroscopes or 3D accelerometers to distinguish larger body movements, such as tossing and turning, from smaller movements, such as breathing. In some examples, the disposable or reusable sensor can monitor the presence of feces and/or urine by detecting an impedance between one or more electrode arrays within the disposable sensor. The data recorded by the permanent device and disposable sensor can be stored and transmitted to a mobile device, base station, or other electronic device. Parents and caretakers can not only use the instant information to attend to the needs of infants, patients, elderly and special needs individuals, but stored data can also be used to identify certain patterns such as defecation or urination frequency or sleep cycles.

Figure 1:
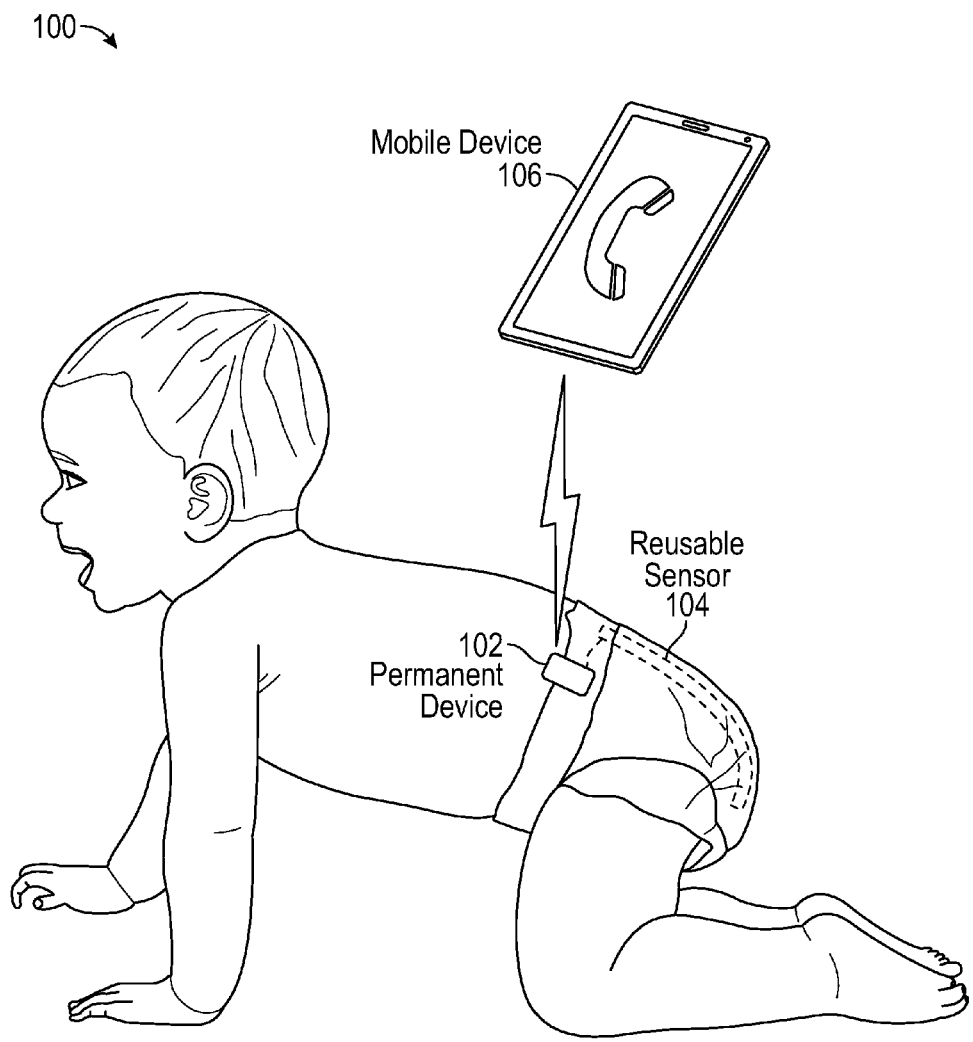
FIG. 1 illustrates an example monitoring system that includes a disposable or reusable sensor connected to a permanent device that is capable of wirelessly transmitting information to a mobile device.

FIG. 1 illustrates an example monitoring system 100 that includes a permanent device 102 connected to a disposable or reusable sensor 104. In the example of FIG. 1, the permanent device 102 can wirelessly transmit information to a mobile device 106. However, it should be understood that in other examples, the permanent device 102 can transmit information using wires, and the device 106 can be any type of electronic device capable of receiving and processing the information.

Figure 2:
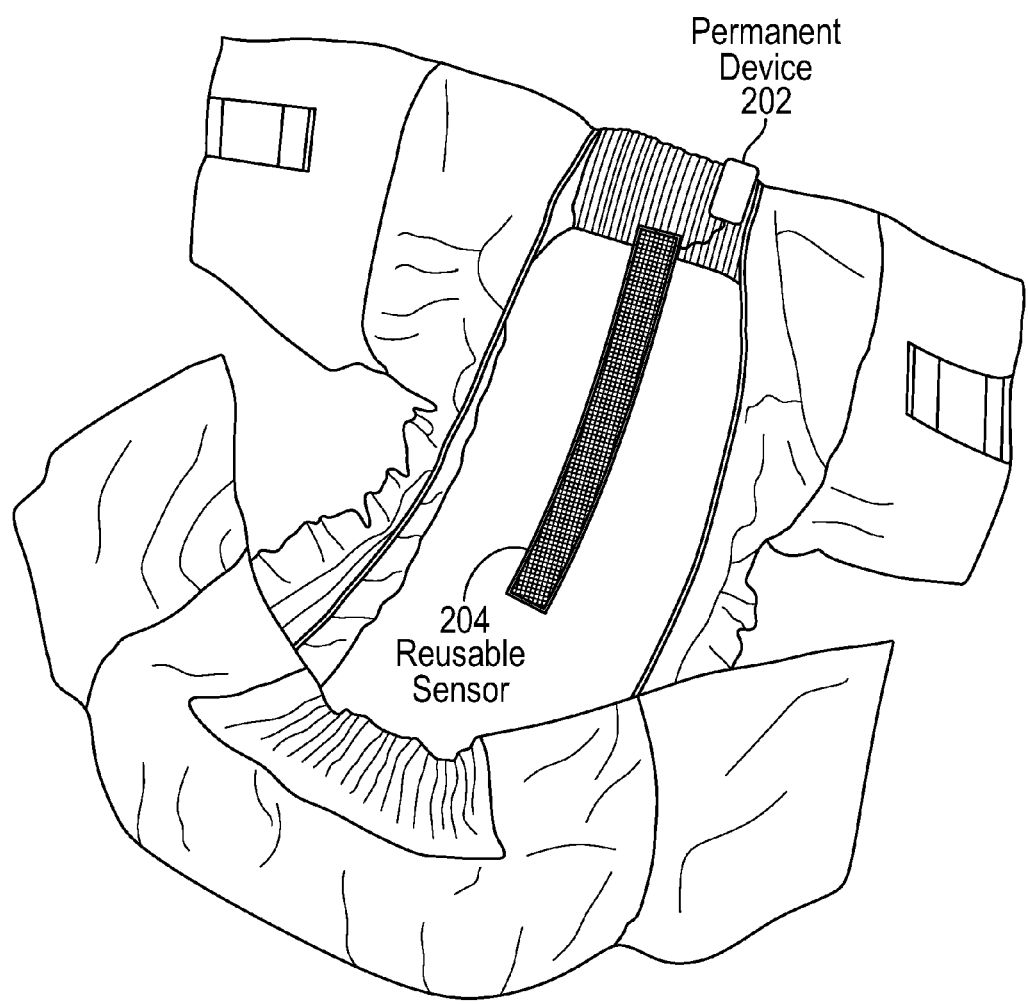
FIG. 2 illustrates an example placement of the monitoring system in an infant's diaper.

FIG. 2 illustrates an example placement of a monitoring system in an infant's diaper (or alternatively an adult diaper). Although FIG. 2 illustrates a disposable or reusable sensor 204 located central to the diaper, in other examples the disposable or reusable sensor may be configured such that an alternative placement is desirable. In addition, although FIG. 2 illustrates a permanent device 202 secured to an upper back portion of the diaper, in other examples the permanent device may be configured such that an alternative placement is desirable.

Figure 3:
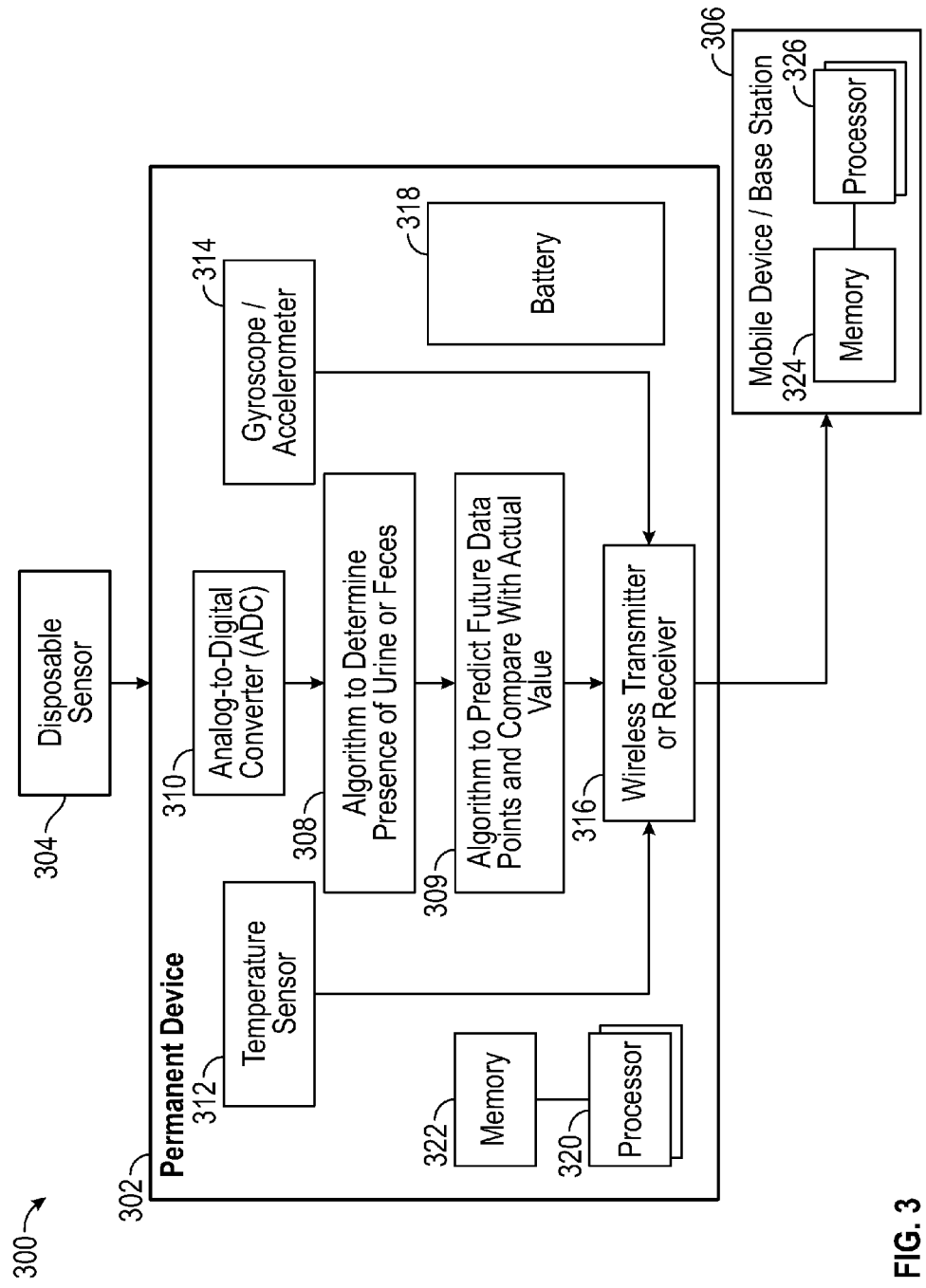
FIG. 3 is a block diagram of an example monitoring system according to examples of the disclosure.

FIG. 3 is a block diagram 300 of an example monitoring system according to examples of the disclosure. In the example of FIG. 3, a disposable or reusable sensor 304 can include a plurality of electrodes in one or more electrode arrays that can be used to detect and/or measure the presence of waste material such as feces, urine or other liquids or solids. Permanent device 302 can include an analog-to-digital converter 310 to convert analog information from the disposable sensor into digital form, and store this digital data into a memory 322. One or more algorithms 308 stored in memory 322 can be executed by one or more processors 320 within the permanent device to determine whether feces or urine is present, and in some examples, a measure of how much is present. One or more predictive algorithms 309 stored in memory 322 can be executed by one or more processors 320 within the permanent device to determine future data points from past data points and compare them with actual data values. The information can be used to determine the frequency at which to transmit data to a mobile device, base station, or electronic device 306. However, it should be understood that in other examples, the permanent device 302 may not process any data, but rather may merely transmit the data to a mobile device, base station or other electronic device 306. Device 306 can store the data into memory 324, and execute one or more algorithms stored in the memory using one or more processors 326 to perform various analyses or provide various notifications. The disposable or reusable sensor 304 can be removably connected to the permanent device 302 for easy replacement, recharging, or cleaning. It should be understood that in some examples, the sensor 304 can be disposable, but in other examples, the sensor can be configured to be washable or capable of being sterilized. The permanent device 302 may include, but is not limited to, (1) one or more temperature sensors 312, such as thermistors, thermocouples, or infrared temperature readers, or one or more arrays of such sensors; (2) one or more gyroscopes or accelerometers 314; (3) a wireless or wired transmitter and receiver 316; and (4) a battery 318. In some examples, however, a temperature sensor may alternatively or additional be located in the disposable or reusable sensor. The wireless transmitter and receiver 316 may be used to transmit stored data from the sensors to a mobile device, base station, or other electronic equipment 306 using Bluetooth, ANT+, WiFi, NFC, RFID or other wireless communication methods, or receive information from the mobile device, base station or other electronic equipment using Bluetooth, ANT+, WiFi, NFC, RFID or other wireless communication methods. Hardwire transfer and reception of stored data may also be used.

Figure 4:
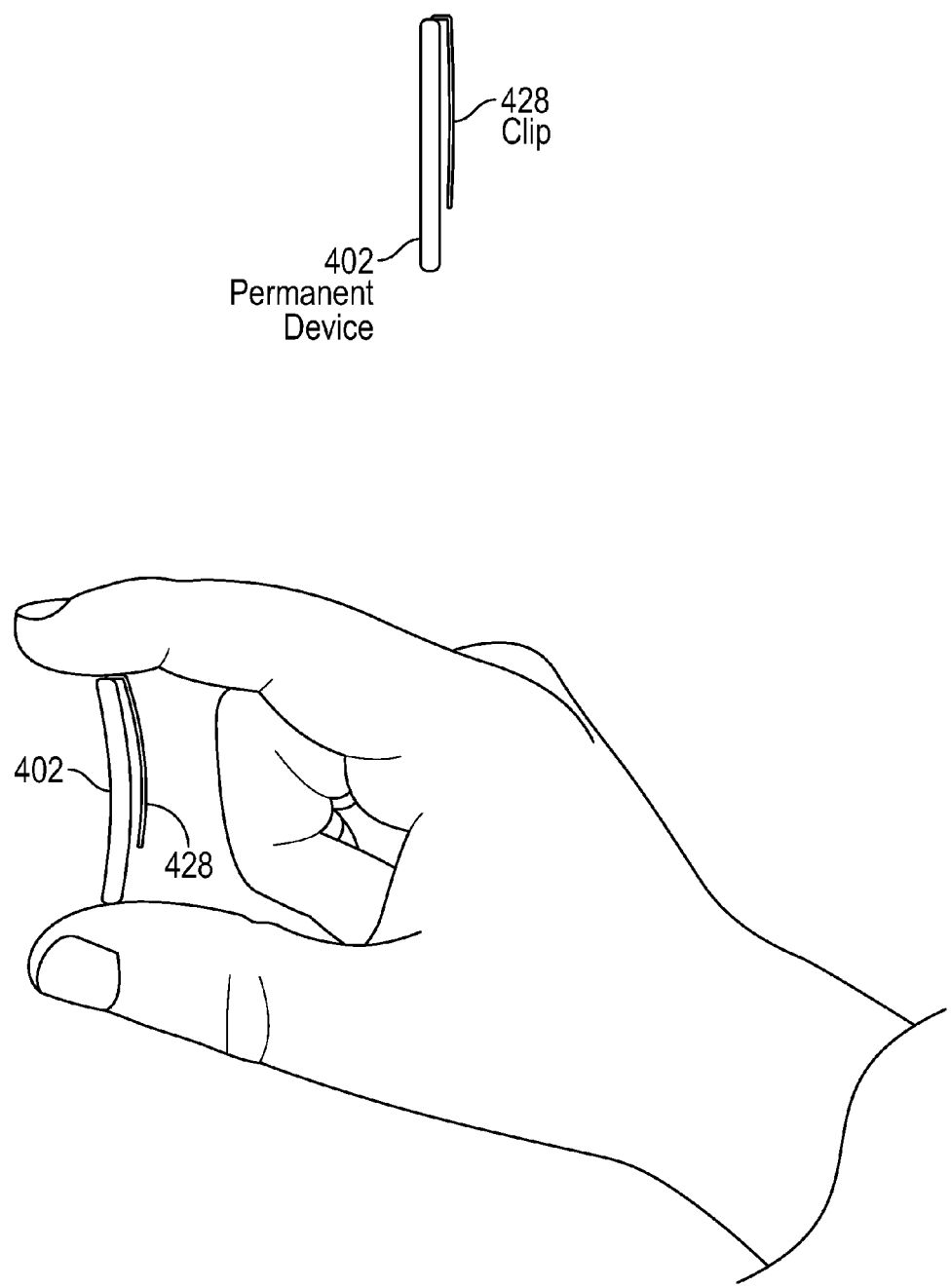
FIG. 4 is an example permanent device with a vertical design, made of flexible material.

FIG. 4 is an example permanent device 402 with a vertical design and a clip 428. The permanent device 402 (or at least a substrate and outer layers within the permanent device 402) can be made of flexible material or can be hinged so that an infant, patient, or elderly individual can comfortably wear the device without noticing it, for example, while rolling over.

Figure 5:
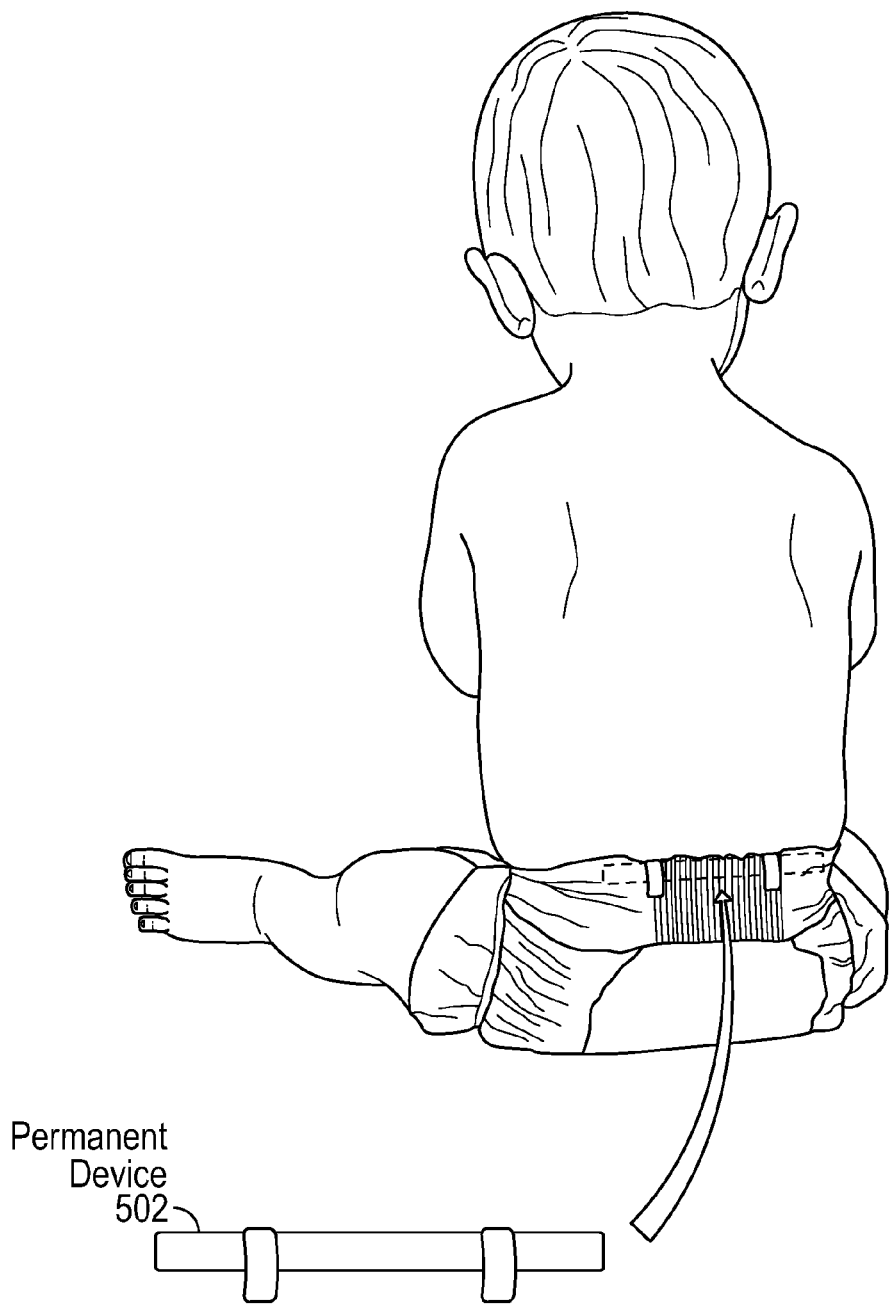
FIG. 5 is an example permanent device with a horizontal design, made of flexible material.

FIG. 5 is an example permanent device 502 with a horizontal design. The permanent device 502 can be made of flexible material or can be hinged so that an infant, patient, or elderly individual can comfortably wear the device without noticing it, for example, while rolling over.

Figure 6A:
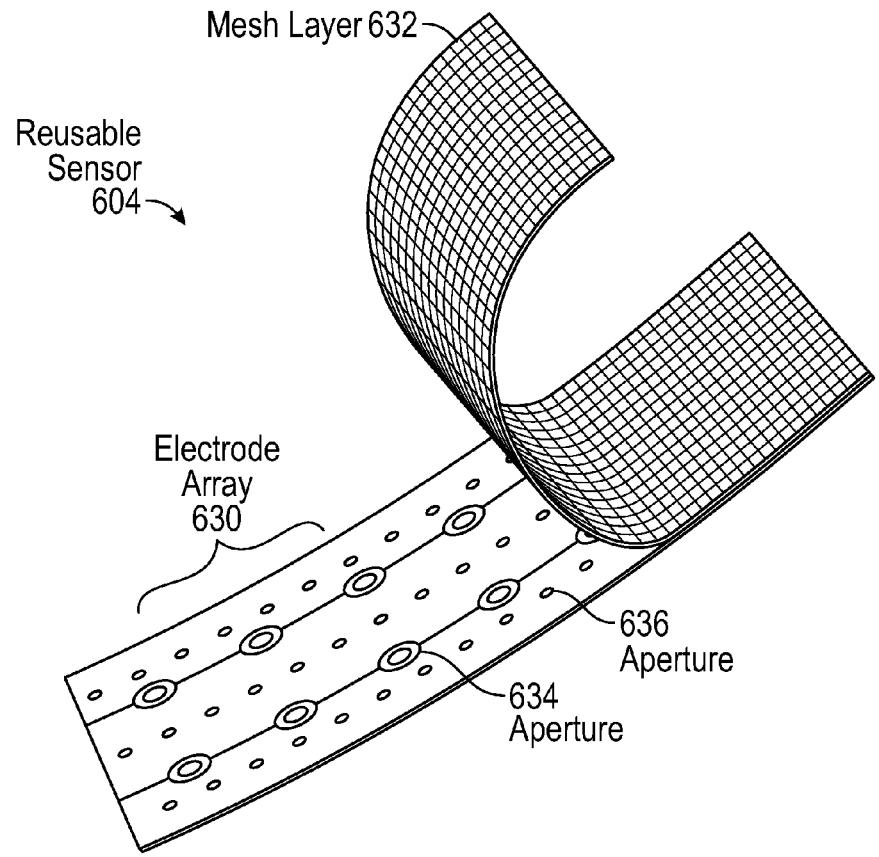
FIG. 6a is an exploded, perspective view of an example disposable or reusable sensor according to some examples of the disclosure.

FIG. 6a is a perspective view of an example disposable or reusable sensor 604 according to some examples of the disclosure. In some examples, the disposable or reusable sensor 604 can include one or more electrode arrays 630 on the bottom layer of the sensor, away from the body. An electrically insulating mesh layer 632 can cover the one or more electrode arrays to insulate them from the skin of an infant, patient, or elderly individual. The mesh layer spacing may be 0.01 mm-0.1 mm, 0.1 mm-1 mm, or 1 mm-10 mm, in some examples. In some examples, the one or more electrode arrays can have one or more holes or apertures 634 in the middle of each electrode (e.g., ring-shaped) to allow liquid or other material to pass through quickly. In addition, one or more additional holes or apertures 636 can be arranged near the electrode arrays to make the membrane even more permeable to liquid or solid material.

Figure 6B:
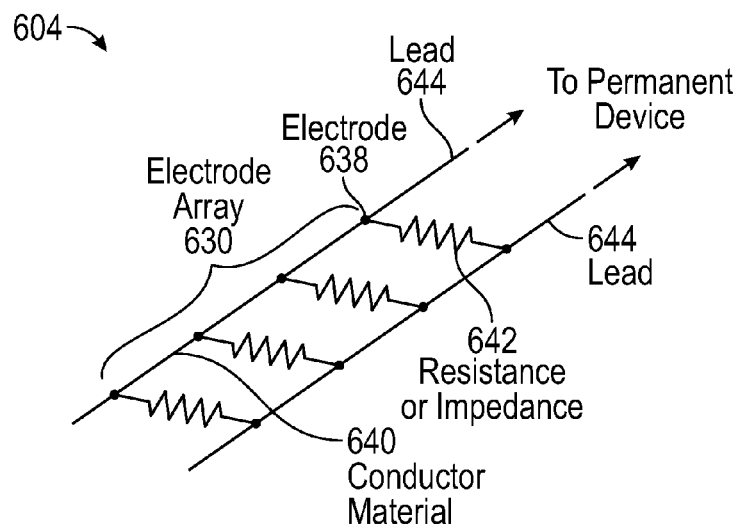
FIG. 6b is an example electrical circuit diagram of the example disposable or reusable sensor of FIG. 6a according to some examples of the disclosure.

FIG. 6b is an example electrical circuit diagram of the example disposable or reusable sensor 604 of FIG. 6a according to some examples of the disclosure. In the example of FIG. 6b, each electrode array 630 can include one or more electrodes 638 that can be exposed at least on the side facing away from the insulating layer (not shown in FIG. 6b). Each electrode 638 can be electrically connected by a wire or strip of conductive material 640 that may be insulated. When waste products such as feces or urine comes into contact with the electrode array 630, a resistance or impedance 642 can be formed between various electrodes 638. Note that although FIG. 6b shows a resistance or impedance 642 forming only between adjacent electrodes 638, it should be understood that depending on the location and amount of waste, a network of resistances and impedances can be formed between any number of electrodes 638. The resistances or impedances between electrodes 638 can form a net resistance or impedance between the two leads 644 of the electrode array 630 that can be measured. It should also be understood that the circuit diagram of FIG. 6b is but one example implementation of an electrode array. In other examples, the electrode array can be capacitively coupled, and the presence of waste material can cause a change in the amount of capacitance between leads on the electrode array. This change in capacitance can also be detected and measured.

Figure 7:
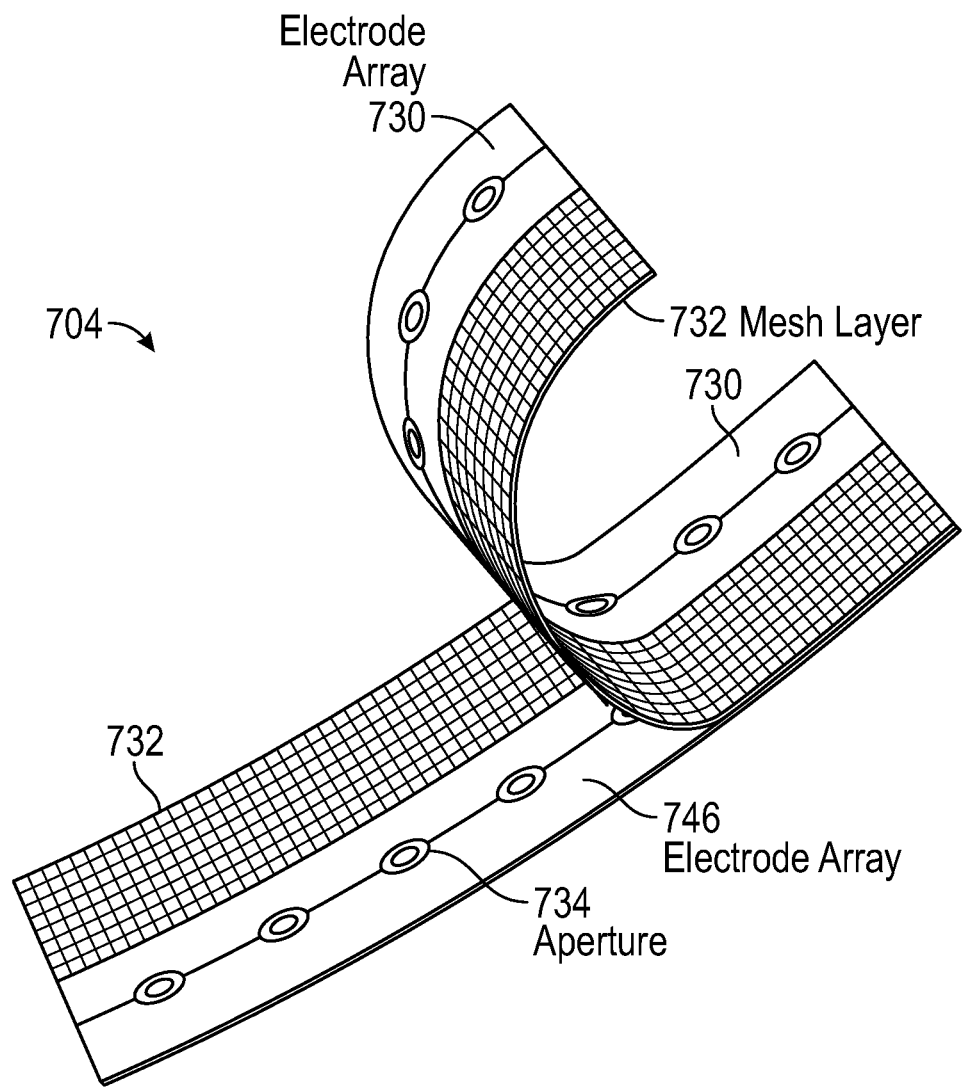
FIG. 7 is an exploded, perspective view of another example disposable or reusable sensor according to some examples of the disclosure.

FIG. 7 is a perspective view of another example disposable or reusable sensor 704 according to some examples of the disclosure. In some examples, the disposable or reusable sensor 704 can include one or more electrode arrays 730 on the top layer, and one or more electrode arrays 746 on the bottom layer. The electrode arrays can be staggered or offset so as to not rest upon each other. The other part of each layer can be a mesh 732 that can cover the electrode portion of the other layer, insulating the electrodes from the skin of an infant, patient, or elderly individual. The mesh layer spacing may be 0.01 mm-0.1 mm, 0.1 mm-1 mm, or 1 mm-10 mm. In some examples, the one or more electrode arrays can have one or more holes or apertures 734 in the middle of each electrode (e.g., ring-shaped) to allow liquid or other material to pass through quickly.

In various examples of the disclosure, pre-programmed or a fixed current or voltage can be applied to the one or more electrode arrays and can be used to calculate impedance, resistance, voltage, and the like, and/or detect changes to these parameters in the presence of conductive waste material such as feces or urine. For example, because the presence of feces creates a lower resistance or impedance path between electrodes, increasing amounts of feces can cause lower resistance or impedance paths between electrodes, lowering the net impedance or resistance between the electrodes in the electrode array. Applied current or voltage can be either alternating (AC) or direct (DC). Applied voltages may be between 0.000V-0.005V RMS, 0.005V-0.05V RMS, 0.05V-0.5V RMS, or 5V-50V RMS. The frequency of applied voltage may be between 0.1 Hz-1 Hz, 10 Hz-100 Hz, 100 Hz-1,000 Hz, 1,000 Hz-10,000 Hz, 10,000 Hz-100,000 Hz, or 100,000 Hz-1,000,000 Hz when the applied signal is AC. In some examples, a resistor, capacitor, inductor, or other electrical component can comprise part or all of the sensor circuitry. For example, a resistor, capacitor, or inductor can be connected in parallel or in series with the electrode arrays to determine whether the electrode arrays are electrically open or closed. Impedance or other values can be converted using an analog-to-digital convertor (ADC), and in some examples an algorithm can be executed by one or more processors to process data and determine the presence of feces or urine.

In some examples of the disclosure, a silver-silver chloride counter electrode can be used in conjunction with an ammonia-selective membrane covering a working electrode. Ammonia is commonly found in urine, and an ammonia-selective membrane can allow only ammonia to pass through and come in contact with the working electrode. A device that detects the potential difference between the working electrode and the silver-silver chloride counter electrode can then be used to detect the presence of urine. In some examples, similar membranes that are selective for chemical compounds found in feces (e.g., $H_2S$) can be used to cover the working electrode. When used in conjunction with the silver-silver chloride counter electrode, the presence of feces can be detected.

Some examples of the disclosure can use amperometry to detect the presence of chemical species. In such examples, a working electrode can be composed of an electrochemically inert metal such as carbon, gold, or platinum. A reference electrode can be composed of silver-silver chloride. A voltage between 0.01-0.1V or 0.1-1V, for example, can be applied between the working and reference electrodes. A membrane that is selective for certain chemical species, as discussed above, can be used to fully cover the working electrode and allow the passage of only certain chemical species. In some examples, an enzyme that is reactive with the chemical species can be applied between the membrane and working electrode. The chemical reaction product(s) can be oxidized or reduced at the working electrode, giving rise to a current. This current, or a corresponding parameter, can be measured to detect the presence of the chemical species.

Figure 8:
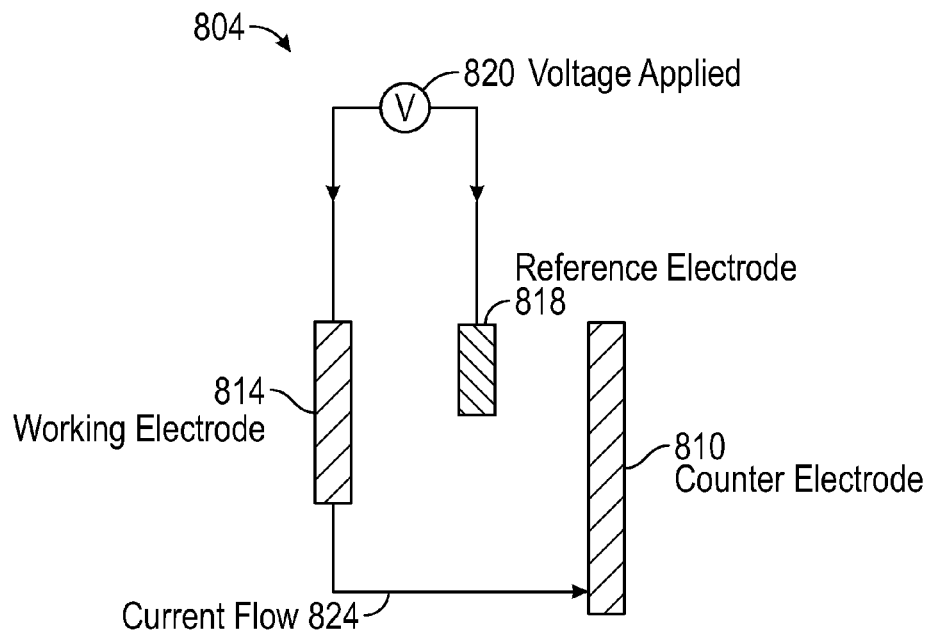
FIG. 8 is a block diagram of an example counter electrode working in conjunction with a working electrode and reference electrode according to examples of the disclosure.

FIG. 8 illustrates an example block diagram of the use of amperometry. A counter electrode 810 can be used in conjunction with the working electrode 814 and reference electrode 818. The counter electrode 810 can be the same material as the working electrode 814 or another electrochemically inert gas. A constant voltage 820 is applied between the working and reference electrodes. The current 824, however, flows only between the working and counter electrodes.

Figure 9:
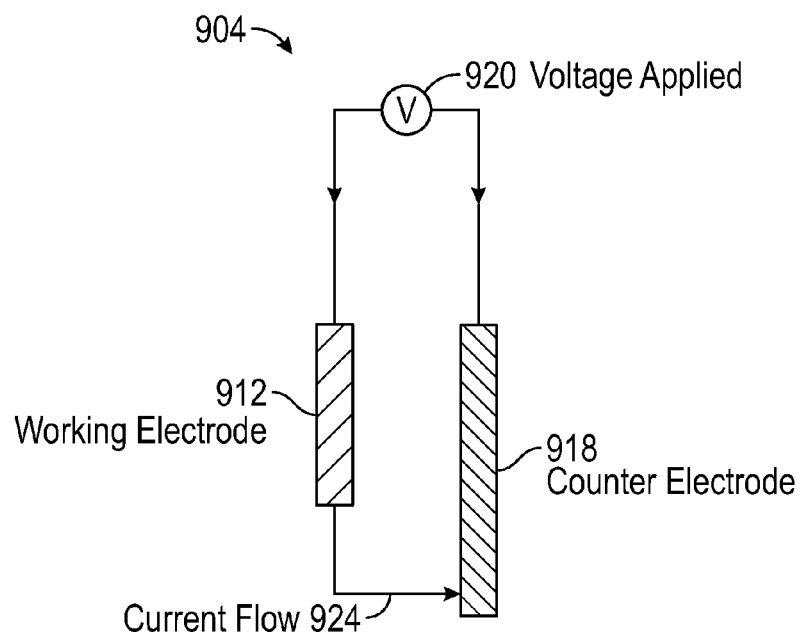
FIG. 9 is a block diagram of the use of direct potentiometry to detect chemical species according to examples of the disclosure.

FIG. 9 illustrates an example block diagram of the use of direct potentiometry to detect chemical species. A counter electrode 918 can be used in conjunction with a working electrode 912. A constant voltage 920 is applied between the counter electrode 918 and working electrode 912. The current 924 flows between the working electrode and counter electrode.

Impedance values from the disposable or reusable sensor, temperature data, gyroscope or accelerometer data, or other readings can be stored in the permanent device. In some examples, data stored in the permanent device can be processed in the permanent device to determine the presence of urine or feces, determine body temperature, body posture, breathing frequency, and resting quality, or determine other qualities of the individual being monitored. In some other examples, data stored in the permanent device can be wirelessly transmitted using Bluetooth, WiFi, or RFID to a mobile device, base station or other electronic device for processing to determine the presence of urine or feces, determine body temperature, body posture, breathing frequency, and resting quality, or determine other characteristics of the individual being monitored. In some examples, processed data can then be passed on to other programs or processors for downstream use.

The transmission of data to the permanent device, or to the mobile device, base station or other electronic device may occur continuously, periodically according to a predetermined schedule, or occur in accordance with the detection of a particular event. For example, when a low impedance is detected between the electrodes in an electrode array, another measurement may be initiated shortly after to confirm the low impedance is indeed caused by feces, instead of urination.

Post-processing of the stored data, regardless of where it is performed, can include determining not only the presence of urine or feces, but also an estimated amount based on the stored resistance or impedance readings. Various thresholds can be used to quantify the estimated amount of urine or feces. A timer can track when urine or feces was first detected, and can cause one or more alarms or notifications to be presented at the remote mobile device, base station, or other electronic device based on the amount of time that has elapsed. Post-processing can also include analyzing motion data to determine other characteristics. For example, motion data can be tracked over time to determine when, and for how long, the wearer is sleeping on their back, front, side, etc., or provide a measure of resting quality (e.g., movement within one or more thresholds within a particular period of time can be used to determine whether the wearer is sleeping soundly, or is restless). In another example, motion data can be tracked over time, and the periodicity of the motion data can be used to determine the wearer's breathing frequency. Larger body movement may indicate that the wearer is tossing and turning, while smaller body movements can be associated with the wearer's breathing. An algorithm can be used to separate these two types of movements and make determinations accordingly.

Impedance values from the disposable or reusable sensor, temperature data, gyroscope or accelerometer data, or other readings can also be used in conjunction with one another to detect patterns. In some examples, patterns between body movements and the presence of urine or feces can be established. For example, the detection of urine or feces combined with the detection of increased wearer movement can be used to trigger a notification or alarm indicating one or both of (1) an amount of urine or feces and (2) a "discomfort level." In other examples, impedance values from the disposable sensor, temperature data, gyroscope or accelerometer data, or other data can be used in conjunction with external input to detect patterns. For instance, in some examples, a user can input the calorie intake of an infant, patient or elderly individual before bedtime. A pattern between calorie intake and frequency of defecation may be established. A user can then utilize this pattern to adjust the calorie intake to minimize defecation during sleeping hours while preventing hunger-induced waking.

Figure 10:
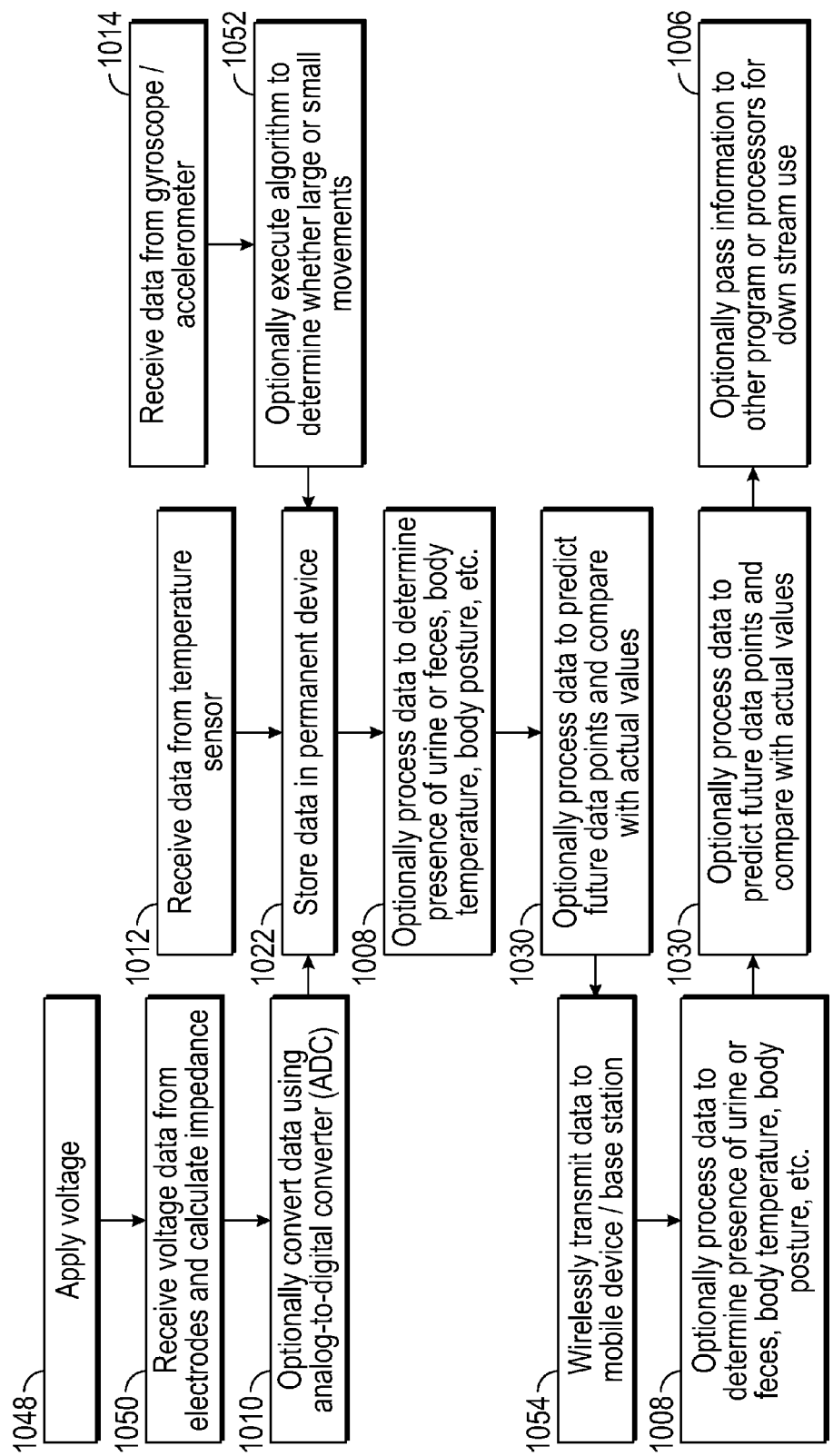
FIG. 10 illustrates an exemplary flow chart for monitoring defecation, urination, near-body temperature, body posture, and body movements of infants, patients, special needs and elderly individuals, and communicating the information via wireless technology to mobile devices or base stations according to some examples of the disclosure.

FIG. 10 illustrates an exemplary flow chart 1046 for monitoring defecation, urination, near-body temperature, body posture, body movements and other vital signs or characteristics of infants, patients, special needs and elderly individuals, and communicating the information via wireless technology (though wired technology can be used as well) to mobile devices, base stations or other electronic devices according to some examples of the disclosure. First, voltage (or current) can be applied through the battery-powered permanent device to the one or more electrode arrays in the disposable or reusable sensor at 1048. Applied voltage or current can be either alternating (AC) or direct (DC). Voltage (or current) data from the sensors can then be received at 1050 and used to calculate impedance. Impedance (I) can be calculated by dividing voltage (V) by resistance (R) [I=V/R]. In some examples, impedance data can then be converted using an analog-to-digital converter (ADC) at 1010. In some examples, temperature data can be received at 1012. In some examples, gyroscope, accelerometer or other motion data can be received at 1014. In some examples, gyroscope, accelerometer or other motion data can be analyzed in the permanent device to determine whether body movements are large (e.g., movements such as tossing or turning), or small (e.g., movements such as breathing) at 1052. Impedance data, temperature data, gyroscope or accelerometer data, or other data can be received and stored in the permanent device at 1022. In some examples, data stored in the permanent device can optionally be processed to determine the presence of urine or feces, determine body temperature, body posture, breathing frequency, resting quality or determine other vital signs or characteristics at 1008. In some examples, data stored on the permanent device can optionally be processed to predict future data points and values based on past data points at 1030. The predicted values can then be compared with actual values. In some examples, future data points and values can be predicted using polynomial least squares fitting. For example, the polynomial function can be written as: $y = a_0 + a_1 x + \ldots + a_k x^k$, or in matrix form as:

$$\begin{bmatrix} 1 & x_1 & \cdots & x_1^k \\ 1 & x_2 & \cdots & x_2^k \\ \vdots & \vdots & \ddots & \vdots \\ 1 & x_n & \cdots & x_n^k \end{bmatrix} \begin{bmatrix} a_0 \\ a_1 \\ \vdots \\ a_k \end{bmatrix} = \begin{bmatrix} y_0 \\ y_1 \\ \vdots \\ y_k \end{bmatrix}$$

where "n" represents the number of data points on which the predicted future value is based, "k" represents the order of the polynomial function, and "a" represents the polynomial coefficients of the polynomial fitting function. The difference between the predicted values and actual values can be used to determine the frequency at which to transmit data. Impedance data, temperature data, gyroscope, accelerometer data, or other data are wirelessly transmitted to a mobile device, base station or other electronic device at 1054 (although it should be understood that in other examples, the data may be transmitted via a wired connection). In some examples, data stored in the permanent device can optionally be processed to determine the presence of urine or feces, body temperature, body posture, breathing frequency, resting quality, or other characteristics at 1008. In some examples, impedance data, temperature data, gyroscope data, accelerometer data, or other data can be passed to other programs or processors for downstream use at 1006.

Figure 11:
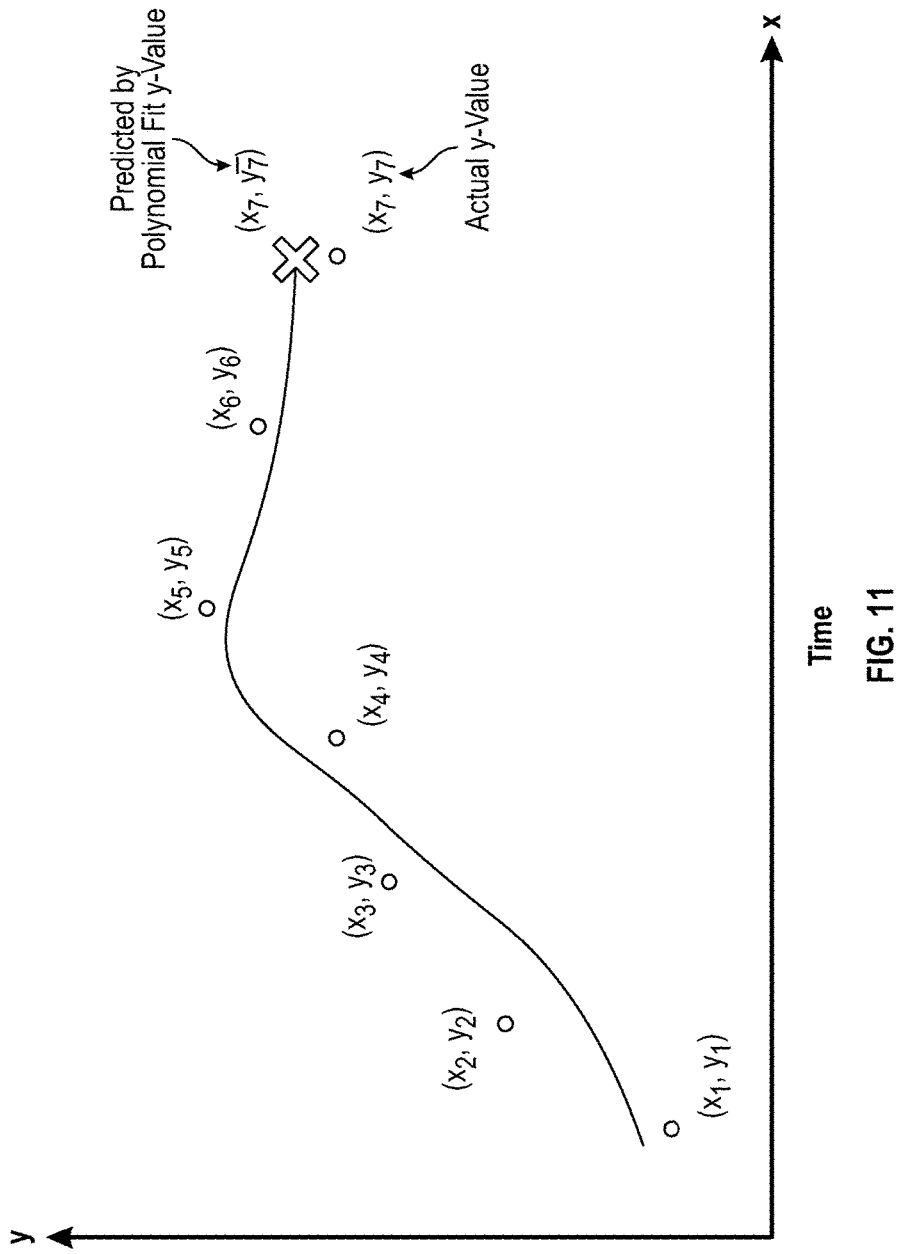
FIG. 11 illustrates an exemplary graph of a polynomial fit used to predict future data point values according to examples of the disclosure.

FIG. 11 illustrates an exemplary graph of a polynomial fit used to predict future data point values. The frequency of the transmission of data to a mobile device or base station can be reduced to conserve energy or accommodate limited bandwidth of devices. In some examples, the predicted future value is compared to the actual value measured and if the difference is small, data transmission is turned off, thus conserving energy (e.g., if $\dfrac{|\bar{y}_7 - y_7|}{y_7} < \delta$, where δ can be less than 10%, data transmission is turned off). If the difference between the predicted future value and the actual measured value is above a certain threshold, the data transmission continues and the actual measured value is transmitted.

Therefore, according to the above, some examples of the disclosure are directed to a system for detecting waste material comprising: one or more sensors configured to change one or more parameters in the presence of the waste material, and a first device communicatively coupled to the one or more sensors and configured for receiving first data from the one or more sensors associated with the change in the one or more parameters and transmitting second data associated with the first data; wherein the second data is indicative of detected waste material. Alternatively or additionally to one or more of the examples disclosed above, in some examples, the one or more sensors further comprise at least two layers, with a plurality of electrodes formed on one of the at least two layers. Alternatively or additionally to one or more of the examples disclosed above, in some examples, the one or more sensors further comprise at least two layers, with a plurality of electrodes formed on different ones of the at least two layers and staggered so as to not rest upon each other. Alternatively or additionally to one or more of the examples disclosed above, in some examples, the one or more sensors further include a plurality of electrodes formed with apertures to allow liquid or other substances pass through. Alternatively or additionally to one or more of the examples disclosed above, in some examples, the first device further includes at least one of a motion sensing mechanism and a temperature sensing mechanism, and the second data further includes at least one of motion data and temperature data. Alternatively or additionally to one or more of the examples disclosed above, in some examples, the system further comprises a second device for receiving the second data from the first device and generating a notification based on the second data. Alternatively or additionally to one or more of the examples disclosed above, in some examples, at least one of the first and second devices further includes at least one processor capable of determining at least one of body posture or movement. Alternatively or additionally to one or more of the examples disclosed above, in some examples, the one or more sensors further includes a silver-silver chloride counter electrode used in conjunction with a chemical-sensitive membrane covering a working electrode, the one or more sensors capable of detecting particular chemicals present in urine or feces. Alternatively or additionally to one or more of the examples disclosed above, in some examples, the working electrode is further composed of an electrochemically inert metal, and further comprising an enzyme that is reactive with chemical species disposed between the membrane and working electrode, wherein the working electrode is configured such that chemical reaction products oxidized or reduced at the working electrode give rise to a measurable current. Alternatively or additionally to one or more of the examples disclosed above, in some examples, the permanent device is flexible. Alternatively or additionally to one or more of the examples disclosed above, in some examples, at least one of the first and second devices further includes at least one processor capable of determining breathing frequency. Alternatively or additionally to one or more of the examples disclosed above, in some examples, at least one of the first and second devices further includes at least one processor capable of detecting one or more patterns from one or more of the sensor data, temperature data and motion data, and providing information related to one or more patterns. Alternatively or additionally to one or more of the examples disclosed above, in some examples at least one of the first and second devices includes at least one processor capable of determining future data point values based on past data points, and determining data transmission frequency based on the difference between the calculated future data point values and the actual value of measured data.

Some examples of the disclosure are directed to an apparatus for detecting waste material, comprising: a receiving circuit for receiving first data from one or more waste material sensors; at least one of a temperature sensor and a motion sensor for generating temperature data and motion data; and a transmitting circuit for transmitting second data, the second data based on at least one of the first data, temperature data, and motion data.

Some examples of the disclosure are directed to a method of providing an alert regarding a detection of waste material, comprising: detecting the waste material using one or more sensors; communicating first data indicative of the presence of the waste material from the one or more sensors to a first device; transmitting second data associated with the first data from the first device to a second device; and generating an alert at the second device indicative of the detected waste material. Alternatively or additionally to one or more of the examples disclosed above, in some examples, the method further comprises: generating at least one of temperature and motion data at the first device; wherein the second data is indicative of the generated at least one temperature and motion data. Alternatively or additionally to one or more of the examples disclosed above, in some examples, the method further comprises: determining a breathing frequency from the motion data. Alternatively or additionally to one or more of the examples disclosed above, in some examples, the method further comprises determining a data transmission frequency from one or more calculated predicted data point values and the actual measured value of sensor data, temperature data and motion data. Alternatively or additionally to one or more of the examples disclosed above, in some examples, the method further comprises: detecting one or more patterns from one or more of the sensor data, temperature data and motion data, and providing information related to the one or more patterns.

Although examples of this disclosure have been fully described with reference to the accompanying drawings, it is to be noted that various changes and modifications will become apparent to those skilled in the art. Such changes and modifications are to be understood as being included within the scope of examples of this disclosure as defined by the appended claims.

The invention claimed is:
1. A system for detecting waste material comprising:
one or more sensors configured to change one or more parameters in the presence of the waste material that comprises feces or urine, wherein the one or more sensors comprise a working electrode and a silver-silver chloride counter electrode, wherein the silver-silver chloride counter electrode comprises an ammonia-selective membrane covering and the working electrode comprises a hydrogen sulfide-selective membrane covering, and
a first device communicatively coupled to the one or more sensors and configured for receiving a first data from the one or more sensors associated with the change in the one or more parameters and transmitting a second data associated with the first data;
wherein the second data is indicative of detected waste material.

2. The system of claim 1, wherein the one or more sensors comprise at least two layers, with a plurality of electrodes formed on one of the at least two layers.

3. The system of claim 1, wherein the one or more sensors comprise at least two layers, with a plurality of electrodes formed on the at least two layers and staggered so as to not rest upon each other.

4. The system of claim 1, wherein the one or more sensors include a plurality of electrodes formed with apertures to allow liquid to pass through.

5. The system of claim 1, wherein the first device includes at least one of a motion sensing mechanism and a temperature sensing mechanism, and the second data includes at least one of motion data and temperature data.

6. The system of claim 5, further comprising a second device for receiving the second data from the first device and generating a notification based on the second data.

7. The system of claim 6, wherein at least one of the first and second devices includes at least one processor capable of determining at least one of body posture or movement.

8. The system of claim 6, wherein at least one of the first and second devices includes at least one processor configured to detect one or more patterns from the first data or the second data, and providing information related to the one or more patterns.

9. The system of claim 6, wherein at least one of the first and second devices includes at least one processor configured to determine a future data based on a past data, and to determine a data transmission frequency based on a difference between the future data and a measured data.

10. The system of claim 1, wherein the working electrode is composed of an electrochemically inert metal, and further comprises an enzyme that is reactive with chemical species disposed between the hydrogen-sulfide selective membrane and the working electrode, wherein the working electrode is configured such that chemical reaction products oxidized or reduced at the working electrode give rise to a measurable current.

11. The system of claim 1, wherein the first device is flexible.

12. The method of claim 1, wherein the first device comprises at least one processor configured to determine breathing frequency.

13. An apparatus for detecting waste material that comprises urine or feces, comprising: a receiving circuit for receiving a first data from one or more waste material sensors, wherein the one or more waste material sensors comprise a working electrode and a silver-silver chloride counter electrode, wherein the silver-silver chloride counter electrode comprises an ammonia-selective membrane covering and the working electrode comprises a hydrogen sulfide-selective membrane covering; at least one of a temperature sensor and a motion sensor for generating temperature data and motion data; a transmitting circuit for transmitting a second data, the second data based on at least one of the first data, temperature data, and motion data.

14. The method of claim 13; wherein the apparatus comprises the motion sensor configured to generate the motion data, wherein the motion data is used to determine a breathing frequency.

15. A method of providing an alert regarding a detection of waste material that comprises urine or feces, comprising: detecting the waste material using one or more sensors, wherein the one or more sensors comprise a working electrode and a silver-silver chloride counter electrode, wherein the silver-silver chloride counter electrode comprises an ammonia-selective membrane covering and the working electrode comprises a hydrogen sulfide-selective membrane covering; communicating a first data indicative of the presence of the waste material from the one or more sensors to a first device; transmitting a second data associated with the first data from the first device to a second device; generating an alert at the second device indicative of the detected waste material; and generating at least one of temperature and motion data at the first device.

16. The method of claim 15, comprising generating the motion data at the first device, and further comprising determining at least one or body posture or movement from the motion data.

17. The method of claim 15, further comprising: determining a data transmission frequency from a future value data and a measured value of the first data, the second data, the temperature data or the motion data.

18. The method of claim 15, further comprising: detecting one or more patterns from the first data, the second data, the temperature data or the motion data, and providing information related to the one or more patterns.

19. The method of claim 15, wherein the method comprises generating the motion data, and wherein the motion data is used to determine a breathing frequency.

* * * * *